United States Patent
Cummins

(10) Patent No.: US 9,974,676 B2
(45) Date of Patent: May 22, 2018

(54) WIRE COLLECTION DEVICE WITH GEARED ADVANTAGE

(71) Applicant: Cook Medical Technologies LLC, Bloomington, IN (US)

(72) Inventor: Sean Cummins, Mungret (IE)

(73) Assignee: Cook Medical Technologies LLC, Bloomington, IN (US)

( * ) Notice: Subject to any disclaimer, the term of this patent is extended or adjusted under 35 U.S.C. 154(b) by 867 days.

(21) Appl. No.: 14/452,124

(22) Filed: Aug. 5, 2014

(65) Prior Publication Data

US 2015/0051688 A1    Feb. 19, 2015

Related U.S. Application Data

(60) Provisional application No. 61/864,154, filed on Aug. 9, 2013.

(51) Int. Cl.
*A61F 2/966* (2013.01)
*A61F 2/95* (2013.01)
*A61M 25/06* (2006.01)

(52) U.S. Cl.
CPC ...... *A61F 2/966* (2013.01); *A61F 2002/9517* (2013.01); *A61M 2025/0681* (2013.01)

(58) Field of Classification Search
CPC .. A61F 2/95; A61F 2/954; A61F 2/958; A61F 2/962; A61F 2/966; A61F 2/97; A61F 2002/9505; A61F 2002/9511; A61F 2002/9517; A61F 2002/9522; A61F 2002/9528; A61F 2002/9534; A61F 2002/9583; A61F 2002/9586;
(Continued)

(56) References Cited

U.S. PATENT DOCUMENTS 706,606 A    8/1902  Spriggs
844,550 A    2/1907  Thomasson
(Continued)

FOREIGN PATENT DOCUMENTS

EP    1 251 796 B1    12/2004
EP    2431009         3/2012
(Continued)

OTHER PUBLICATIONS

Abbott Laboratories, "Absolute Pro® .035 Biliary Self-Expanding Stent System," obtained at internet address <http://www.abbottvascular.com/docs/ifu/peripheral_intervention/eIFU_absolute_pro_35_Billary_SelfExpanding_Stent_System.pdf>, EL2070955, dated Jul. 24, 2009, 11 pages.

*Primary Examiner* — Kathleen Holwerda
*Assistant Examiner* — Socrates L Boutsikaris
(74) *Attorney, Agent, or Firm* — Brinks Gilson & Lione

(57) ABSTRACT

A stent delivery system includes a wire collection device which is constructed with a thumbwheel coupled to a collection spindle that is rotatable to collect a retraction wire about the collection spindle. A proximal end of an outer stent-constraining sheath is coupled to the collection spindle by the retraction wire and a distal end of the outer sheath retractably surrounds a distally-disposed self-expanding stent. The wire collection device includes a first set of gears at a higher gear ratio and a second set of gears at a lower gear ratio. Stent deployment speed may be controlled or varied by switching or alternating between engaging the first of gears and the second set of gears, thereby accommodating changing resistance as the outer sheath is retracted and releases binding force of the stent.

17 Claims, 6 Drawing Sheets

(58) Field of Classification Search
CPC .......... A61F 2002/9665; A01K 89/004; A01K 89/00; A01K 89/0105; A01K 89/0106; A01K 89/0183; A01K 89/0184; A01K 89/0185; A01K 89/01902
USPC .............. 623/1.11, 1.12, 2.11; 606/200, 108
See application file for complete search history.

(56) References Cited

U.S. PATENT DOCUMENTS

| | | |
|---|---|---|
| 1,615,534 A | 1/1927 | Cassel |
| 2,939,680 A | 6/1960 | Powell |
| 3,589,486 A | 6/1971 | Kelch |
| 4,466,576 A | 8/1984 | Simson |
| 4,483,326 A | 11/1984 | Yamaka et al. |
| 5,026,377 A | 6/1991 | Burton et al. |
| 5,088,581 A | 2/1992 | Duve |
| 5,534,007 A | 7/1996 | St. Germain et al. |
| 5,772,669 A | 6/1998 | Vrba |
| 5,904,667 A | 5/1999 | Falwell |
| 5,968,052 A | 10/1999 | Sullivan, III et al. |
| 6,059,813 A | 5/2000 | Vrba et al. |
| 6,190,360 B1 | 2/2001 | Iancea et al. |
| 6,238,402 B1 | 5/2001 | Sullivan, III et al. |
| 6,273,895 B1 | 8/2001 | Pinchuk et al. |
| 6,387,977 B1 | 5/2002 | Sawhney et al. |
| 6,395,017 B1 | 5/2002 | Dwyer et al. |
| 6,520,983 B1 | 2/2003 | Colgan et al. |
| 6,607,551 B1 | 8/2003 | Sullivan et al. |
| 6,660,031 B2 | 12/2003 | Tran et al. |
| 6,773,446 B1 | 8/2004 | Dwyer et al. |
| 6,805,314 B2 | 10/2004 | Hopper |
| 6,860,898 B2 | 3/2005 | Stack et al. |
| 6,884,259 B2 | 4/2005 | Tran et al. |
| 6,905,461 B2 | 6/2005 | Hino |
| 6,939,352 B2 | 9/2005 | Buzzard et al. |
| 7,052,511 B2 | 5/2006 | Weldon et al. |
| 7,122,050 B2 | 10/2006 | Randall et al. |
| 7,300,438 B2 | 11/2007 | Falwell et al. |
| 7,300,456 B2 | 11/2007 | Andreas et al. |
| 7,604,611 B2 | 10/2009 | Falwell et al. |
| 7,615,042 B2 | 11/2009 | Beyar et al. |
| 7,674,282 B2 | 3/2010 | Wu et al. |
| 7,758,625 B2 | 7/2010 | Wu et al. |
| 7,815,669 B2 | 10/2010 | Matsuoka et al. |
| 7,935,141 B2 | 5/2011 | Randall et al. |
| 7,967,829 B2 | 6/2011 | Gunderson et al. |
| 7,976,574 B2 | 7/2011 | Papp |
| 7,993,384 B2 | 8/2011 | Wu et al. |
| 8,025,692 B2 | 9/2011 | Feeser |
| 8,075,606 B2 | 12/2011 | Dorn |
| 8,216,296 B2 | 7/2012 | Wu et al. |
| 8,323,326 B2 | 12/2012 | Dorn et al. |
| 8,337,077 B2 | 12/2012 | Giacobino |
| 8,500,789 B2 | 8/2013 | Wuebbeling et al. |
| 2003/0163085 A1 | 8/2003 | Tanner et al. |
| 2004/0006380 A1 | 1/2004 | Buck et al. |
| 2004/0087979 A1 | 5/2004 | Field |
| 2005/0033403 A1 | 2/2005 | Ward et al. |
| 2005/0149159 A1 | 7/2005 | Andreas et al. |
| 2005/0256452 A1 | 11/2005 | DeMarchi et al. |
| 2005/0256562 A1 | 11/2005 | Clerc et al. |
| 2005/0273151 A1 | 12/2005 | Fulkerson et al. |
| 2006/0259124 A1 | 11/2006 | Matsuoka et al. |
| 2007/0032860 A1 | 2/2007 | Brooks et al. |
| 2007/0055340 A1 | 3/2007 | Pryor |
| 2007/0055342 A1 | 3/2007 | Wu et al. |
| 2007/0088421 A1 | 4/2007 | Loewen |
| 2007/0156225 A1 | 7/2007 | George et al. |
| 2007/0168014 A1 | 7/2007 | Jimenez et al. |
| 2007/0191925 A1 | 8/2007 | Dorn |
| 2007/0219617 A1 | 9/2007 | Saint |
| 2008/0091257 A1 | 4/2008 | Andreas et al. |
| 2008/0188920 A1 | 8/2008 | Moberg et al. |
| 2008/0300574 A1 | 12/2008 | Belson et al. |
| 2008/0319387 A1 | 12/2008 | Amisar et al. |
| 2009/0024133 A1 | 1/2009 | Keady et al. |
| 2009/0099641 A1 | 4/2009 | Wu et al. |
| 2009/0125093 A1 | 5/2009 | Hansen |
| 2009/0210046 A1 | 8/2009 | Shumer et al. |
| 2009/0270969 A1 | 10/2009 | Fargahi et al. |
| 2010/0004606 A1 | 1/2010 | Hansen et al. |
| 2010/0049297 A1 | 2/2010 | Dorn |
| 2010/0076541 A1 | 3/2010 | Kumoyama |
| 2010/0137967 A1 | 6/2010 | Atlani et al. |
| 2010/0145431 A1 | 6/2010 | Wu et al. |
| 2010/0168834 A1 | 7/2010 | Ryan et al. |
| 2010/0174290 A1 | 7/2010 | Wüebbeling et al. |
| 2011/0295354 A1 | 12/2011 | Bueche et al. |
| 2012/0022635 A1 | 1/2012 | Yamashita |
| 2012/0041537 A1 | 2/2012 | Parker et al. |
| 2012/0059448 A1 | 3/2012 | Parker et al. |
| 2012/0101562 A1 | 4/2012 | Gunderson et al. |
| 2012/0123516 A1 | 5/2012 | Gerdts et al. |
| 2012/0143304 A1 | 6/2012 | Wübbeling et al. |
| 2012/0158117 A1 | 6/2012 | Ryan |
| 2012/0158120 A1 | 6/2012 | Hacker et al. |
| 2012/0296409 A1 | 11/2012 | Kawakita |
| 2012/0330401 A1 | 12/2012 | Sugimoto et al. |
| 2013/0013047 A1 | 1/2013 | Ramos et al. |
| 2013/0018451 A1 | 1/2013 | Grabowski et al. |
| 2013/0110223 A1 | 5/2013 | Munsinger et al. |
| 2014/0188209 A1 | 7/2014 | Loewen |
| 2015/0297378 A1 | 10/2015 | Senness |

FOREIGN PATENT DOCUMENTS

| | | |
|---|---|---|
| WO | WO 94/16762 A1 | 8/1994 |
| WO | WO 2006/014233 A2 | 2/2006 |
| WO | WO 2007/022395 A1 | 2/2007 |
| WO | WO 2007/044929 A1 | 4/2007 |
| WO | WO 2008034793 | 3/2008 |
| WO | WO 2008/124844 A1 | 10/2008 |
| WO | WO 2008/134104 A2 | 11/2008 |
| WO | WO 2010/120671 A1 | 10/2010 |

WIRE COLLECTION DEVICE WITH GEARED ADVANTAGE

CROSS-REFERENCE TO RELATED APPLICATIONS

This application is a non-provisional application which claims priority to U.S. provisional application Ser. No. 61/864,154, filed Aug. 9, 2013, which is incorporated by reference herein in its entirety.

TECHNICAL FIELD

Embodiments disclosed in the present application relate generally to wire collection devices for providing a mechanical advantage in a stent delivery system.

BACKGROUND

Current delivery systems for self-expanding stents generally employ "pin and pull" systems that include an inner catheter extending through an outer sheath. Typically, the stent is placed inside the outer sheath and held in a compressed position by the outer sheath as the outer sheath and inner catheter are inserted into a patient's body vessel. To deploy the stent, the user retracts, or pulls, the outer sheath using one hand while the other hand holds the inner catheter stationary to maintain position of the stent as the outer sheath is retracted, thereby allowing the stent to gradually expand as the outer sheath uncovers the stent.

In these "pin and pull" systems, the user has difficulty maintaining the position of the inner catheter while pulling on the outer sheath because of resistance between the inner catheter and outer sheath, between the outer sheath and the stent, and between the outer sheath and the surrounding vascular walls, or other surrounding blood vessel or body vessel. To overcome this resistance the user may need to exert a large amount of force that leads to various complications, including for example, inaccurate stent positioning, displacement of the stent, shortening or lengthening of the stent, or other damage to the structure of the stent, or damage to the target vessel.

"Pin and pull" systems may also have other disadvantages, including, for example, lack of control during stent deployment and requirement of assistance from a second person. The resistance between the outer sheath and stent varies as more of the stent is uncovered and the stent expands. Specifically, the stent's self-expanding outward circumferential bias frictionally binds it against the outer sheath. During sheath retraction, this binding force decreases as the stent is released, which correspondingly decreases the retraction force needed on the outer sheath. Thus, stent deployment may be difficult to control because the required deployment force varies as the outer sheath retracts across the surface of the stent. As a result, the user must vary the force applied to the outer sheath and the inner catheter in order to maintain a steady deployment speed and ensure accurate stent placement. In most pin and pull systems, the ratio of handle movement to stent deployment distance is 1:1, requiring the user to move faster to deploy longer stents and increasing difficulty in controlling the stent. Because the user's hands are holding the distal ends of the outer sheath and inner catheter, the user cannot easily monitor or attend to the positioning of the outer sheath in the hemostasis valve to ensure accurate stent placement, such that an assistant must be present to attend to the positioning of the outer sheath in the hemostasis valve and accurate positioning of the stent.

Other vascular stent placement delivery systems offer one-handed operation by converting hand-movements into indexed movement of the outer sheath. Such systems generally still operate, however, with a 1:1 ratio of handle movement to stent deployment distance. In other words, such systems do not provide mechanical advantage to accommodate, or reduce the amount of work required for, deployment of longer stents as compared to deployment of shorter stents.

BRIEF SUMMARY

In one aspect, a stent deployment system includes a wire collection device that has a collection spindle, first and second driven gears, a thumbwheel, and first and second actuating gears. The collection spindle can be rotated to collect a retraction wire around the collection spindle, and the retraction wire is coupled to an outer sheath that can be retracted to deploy a stent. The first and second driven gear are mounted along the collection spindle. The second driven gear has a radius greater than the radius of the first driven gear. The thumbwheel is mounted on a wheel axle that is substantially parallel to the collection spindle. The thumbwheel can be rotated and disposed in mechanical communication with the wheel axle so as to actuate rotation of the wheel axle.

In another aspect, a method for deploying a stent using a stent deployment system, such as the one described above, may include turning the thumbwheel in a first position and turning the thumbwheel in a second position. When the thumbwheel is turned in the first position, the first actuating gear engages the first driven gear so as to rotate the collection spindle. This collects the retraction wire at the first speed. When the thumbwheel is turned in the second position, the second actuating gear engages the second driven gear so as to rotate the collection spindle. This collects the retraction wire at the second speed, and preferably requires substantially the same thumbwheel turning force.

In yet another aspect, a wire collection device for a stent deployment system includes a thumbwheel, a wire collection spindle, and a first driven gear and a second driven gear. The thumbwheel is coupled to an axle, and located between the first actuating gear and the second actuating gear, such that the thumbwheel, the first actuating gear, and the second actuating gear can be rotated about a longitudinal axis of the axle. The wire collection spindle can be rotated to collect a retraction wire that is coupled to a proximal end of an outer sheath. The wire collection spindle is located a predetermined distance from the axle. The first and second driven gears are mounted to the wire collection spindle and can be rotated about the longitudinal axis of the wire collection spindle. The radius of the first actuating gear is greater than the radius of the second actuating gear, and the radius of the first driven gear is greater than the radius of the second driven gear. The thumbwheel slide along the longitudinal axis of the axle between a first position and a second position. In the first position, the first actuating gear engages the first driven gear. In the second position, the second actuating gear engages the second driven gear. Sliding the thumbwheel from between the first position and the second position will vary the wire collection speed between a higher speed and a lower speed.

Other systems, methods, features, and advantages of the disclosure will be, or will become, apparent to one with skill in the art upon examination of the following figures and detailed description. It is intended that all such additional systems, methods, features and advantages be included within this description, be within the scope of the invention, and be protected by the claims.

DETAILED DESCRIPTION

Figure 1A:
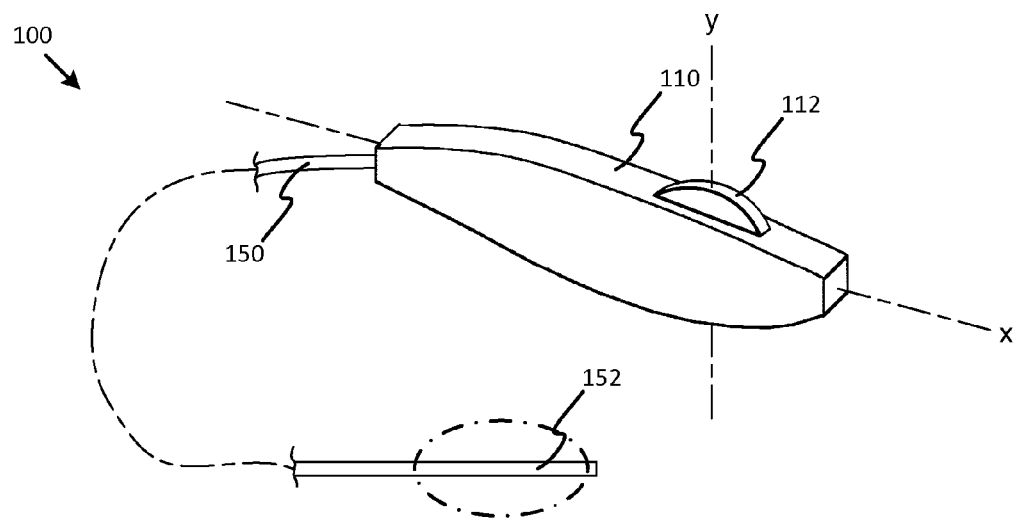
FIG. 1A is a view of an exemplary wire collection device for a stent delivery system.
Figure 1B:
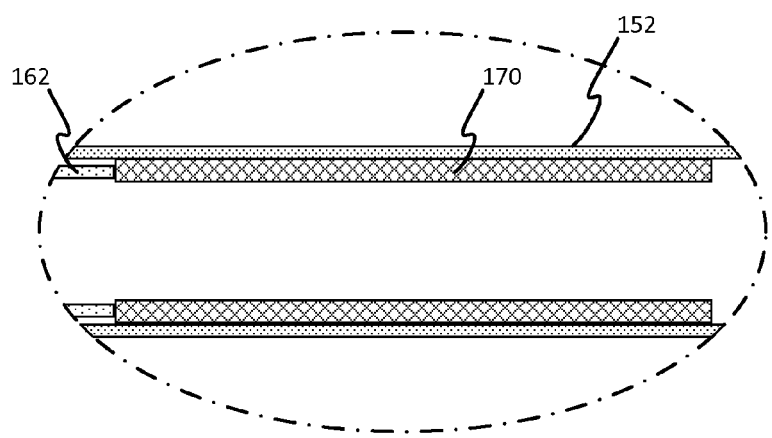
FIG. 1B is a diagrammatic cross-sectional illustration of a detail/partial view of an exemplary wire collection device for a stent delivery system.

Various embodiments are described below with reference to the drawings. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

A wire collection device for a stent delivery system is provided in some embodiments. The stent delivery system includes a retraction wire that is attached at a proximal end to a wire collection device, which is rotatable to pull and collect the retraction wire around a wire collection spindle. The wire collection device includes a thumbwheel that rotates about a wheel axle, a first and second actuating gear, a collection spindle, and a first and second driven gear. As used herein, the terms "first," "second," etc. are used to distinguish one element from another, but do not limit the order, orientation, or configuration of such elements in any way. For example, a first gear may be termed a second gear, and a second gear may be termed a first gear, without departing from the scope of the present disclosure. A user may retract the outer sheath by turning the thumbwheel to actuate rotation of the collection spindle to pull and collect the retraction wire around the collection diameter. The wire collection device allows the user to vary the speed of wire collection by aligning the first actuating gear with the first driven gear or aligning the second actuating gear with the second driven gear. The system may include one or more retraction wires connected by a distal end to the proximal end of the outer sheath, and connected by a proximal end to the wire collection spindle, so that rotation of the collection spindle collects the one or more retraction wires to retract the outer sheath.

A distal end of the retraction wire is connected or attached to a proximal end of an outer sheath that holds a stent at or near a distal end of an inner catheter. The inner catheter extends through the outer sheath from a proximal end near the wire collection device to a distal end near the stent. The stent and the distal ends of the inner catheter and outer sheath are inserted into a body vessel until the stent is located at a desired location. As the thumbwheel is turned, the wire collection device pulls and collects the retraction wire around the collection spindle, thereby retracting the outer sheath across the inner catheter to uncover the stent while the internal catheter holds the stent in the desired location. The stent may be a self-expanding stent, or a stent that is expanded by the force of a balloon.

As used herein, "retraction wire" means a rope, cord, wire, cable, belt, chain, or any other strand(s) of material that is suitable for use in a stent deliver system to retract or pull an outer sheath to allow stent deployment or delivery. The term "collection spindle," as used herein, means one or more axles, spindles, or generally cylindrical structures around which the retraction wire is wound or collected. The wire collection device may be used with one or more retraction wires, and may include one or more collection spindles. As used herein, "collection diameter" refers to the diameter around which a retraction wire collects, or is wound. Thus, the "collection diameter" may increase as the retraction wire overlaps itself as it is being collected, or wound, around an axle, spindle, collection drum, or other cylindrical structure.

When the wire collection device is used with a self-expanding stent, the required deployment force may be greater during initial deployment of the stent and may decrease as the outer sheath uncovers more of the stent. As used herein, "required deployment force" refers to an amount of force required to overcome the frictional forces between the outer sheath and the stent, frictional forces between the outer sheath and an inner catheter that holds the stent in place as the outer sheath is retracted, and frictional forces between the outer sheath and the surrounding body vessels where the stent is being implanted or placed.

The wire collection device may provide the user of the stent delivery system with a more consistent "touch and feel" by reducing the variation in amount of force required from the user to deploy the stent. This may be accomplished by varying the mechanical advantage provided to the user as the required stent deployment force increases, where the mechanical advantage of the wire collection device is determined by the ratio of an actuating gear to a driven gear. More particularly, the mechanical advantage increases as the gear ratio increases. In a system with two sets of gears at a higher and lower gear ratio, the user may begin sheath retraction at a higher gear ratio, when the required deployment force is high, and switch to the lower gear ratio, when the required deployment force decreases. The user may also switch between the two sets of gears at any time during deployment to speed up or slow down deployment.

The wire collection device may provide a mechanical advantage such that the deployment distance, or retraction distance of the outer sheath, increases with hand movements of the user, or revolutions of the thumbwheel. The wire collection device controls retraction of the outer sheath so as to improve user feel and control for accurately positioning the stent. The wire collection device may be configured so that the user may exert a steady, or consistent force, throughout the deployment despite variation in the force required to retract the outer sheath, or deploy the stent. The wire collection device may provide a mechanical advantage to the user that results in a 1:1 ratio, or greater than or less than a 1:1 ratio, of handle movement to stent deployment distance. The gear ratio may be configured according to variation in the required deployment force, the diameter of the thumbwheel, and type of stent.

In some embodiments, as illustrated with reference to FIGS. 1-3, a stent delivery system 100 includes a retraction wire 102 coupled to an outer sheath 104, an inner catheter 106 extending through the outer sheath 104, a wire collection device 108, and a handle 110 housing the wire collection device 108. The handle housing may have a length of about 100 mm (3.9 inches) or greater. The height of the housing may be about 40-50 mm (1.5 to 2.0 inches), and the width of the housing may be about 50 mm (2 inches) or less. A distal end 140 of the retraction wire 102 may be attached, directly or indirectly, to a proximal end 150 of the outer sheath 104 and at or near a proximal end 160 of the inner catheter 106. The proximal end 142 of the retraction wire is attached to the collection spindle 124. The proximal end 160 of the inner catheter 104 is fixed to the handle 110. The distal end 152 of the outer sheath 104 retractably surrounds a stent 170 located at or near a distal end 162 of the inner catheter 106.

Figure 2:
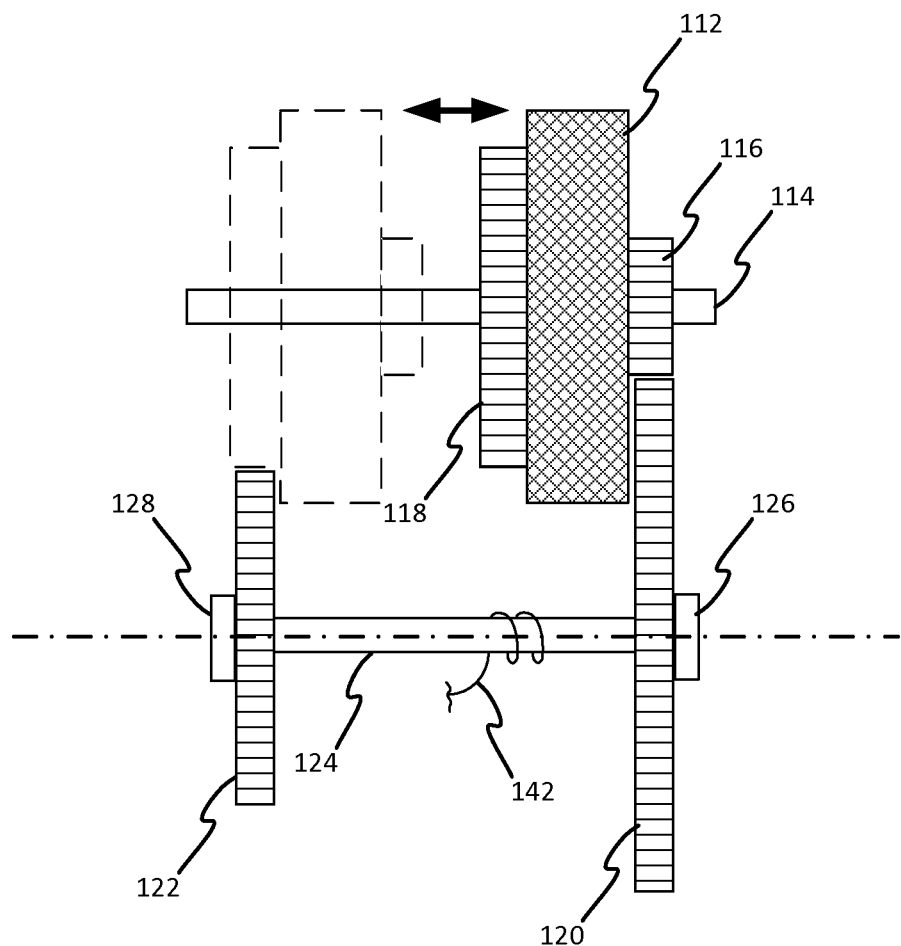
FIG. 2 is a diagrammatic illustration of an exemplary wire collection mechanism in a device for a stent delivery system.
Figure 3:
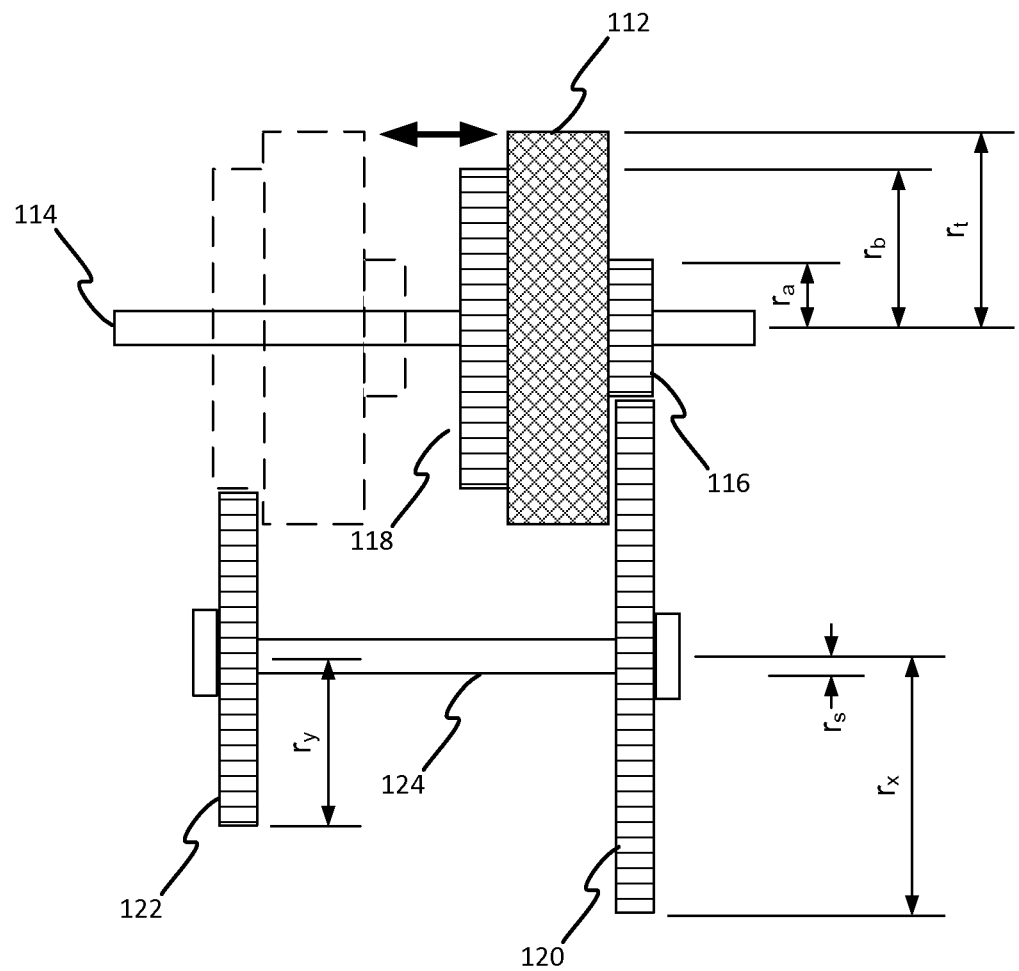
FIG. 3 is a diagrammatic longitudinal cross sectional illustration of a partial view of an exemplary wire collection device for a stent delivery system.

With reference to FIG. 2, the wire collection device 108 includes a thumbwheel 112 mounted on a wheel axle 114 between a first actuating gear 116 and a second actuating gear 118. A first driven gear 120 and a second driven gear 122 are mounted on a collection spindle 124. Shoulders 126, 128 of the collection spindle 124 may keep the driven gears 120, 122 in place as the gears rotate. The collection spindle 124 is substantially parallel to the wheel axle 114. The first actuating gear 116 may have a larger radius than the second driven gear 118. The thumbwheel 112 is slidable along the wheel axle 114 in one direction to align the first actuating gear 116 with the first driven gear 120, and in the opposite direction to align the second actuating gear 118 with the second driven gear 122. Alternatively, the thumbwheel 112 may be fixed to the wheel axle 114, and the wheel axle 114 is slidable from a first position, thereby aligning the first set of gears 116, 120, to a second position, thereby aligning the second set of gears 118, 122. In some embodiments, the collection spindle 124 may be tilted at an angle. Alternatively, the first and second driven gears 120, 122 may be mounted on individual collection spindles that are offset, and the thumbwheel 112 may be movable from side to side along, or together with, the wheel axle 114, or forwards and backwards to align the actuating and driven gear. The thumbwheel 112 and the first and second actuating gears 116, 118 may be adjacent or spaced apart, may be individual components, or may be formed as a unitary piece or component.

When a user turns, or rotates the thumbwheel 112, the wire collection device 108 provides a mechanical advantage to the user that varies depending on whether the user aligns the first set of gears 116, 120 or the second set of gears 118, 122. The mechanical advantage provided depends on the gear ratio, or speed ratio, of each set of gears. For example, with reference to FIG. 3, the first actuating gear 116 has a smaller radius $r_a$ than the radius $r_b$ of the second actuating gear 118; and the first driven gear 120 has a larger radius $r_x$ than the radius $r_y$ of the second driven gear 122. Then the mechanical advantage $MA_1$ provided to the user is the product of the gear ratio of the first set of gears 116, 120 multiplied by the ratio of the radius $r_t$ of the thumbwheel 112 to the radius $r_s$ of the collection spindle 124. In other words, $$MA_1 = (r_x/r_a) \times (r_t/r_s).$$

Similarly, the mechanical advantage $MA_2$ provided by the second set of gears may be expressed as:

$$MA_2 = (r_y/r_b) \times (r_t/r_s).$$

The collection spindle 124 is substantially parallel to the wheel axle 114, such that the sum of the radii, $r_a + r_x$, of the first set of gears 116, 120 is substantially equal to the sum of the radii, $r_b + r_y$, of the second set of gears 118, 122. Thus, the ratio of the mechanical advantage provided by the first set of gears 116, 120 to the mechanical advantage provided by the second set of gears 118, 122 can be approximated as:

$$MA_1/MA_2 = (r_x/r_a)/(r_y/r_b) = (r_x \times r_b)/(r_a \times r_y).$$

Because $r_a$ is less than $r_b$, and $r_y$ is less than than $r_x$, the ratio of the mechanical advantage provided by the first set of gears 116, 120 to the mechanical advantage provided by the second set of gears 118, 122 is greater than 1:1. In other words, $MA_1$ is greater than $MA_2$. When engaging the first set of gears 116, 120, angular velocity $\omega_s$ of the collection spindle 124 is equal to the angular velocity $\omega_x$ of the first driven gear 120, which can be determined as $\omega_x = (r_a \times \omega_a)/r_x$. When engaging the second set of gears 118, 122, the angular velocity $\omega_s$ of the collection spindle 124 is equal to the angular velocity $\omega_y$ of the second driven gear 122, which can be determined as $\omega_y = (r_b \times \omega_b)/r_y$. Thus, for a consistent, or same, amount of force applied to turn the thumbwheel 112, the angular velocity $\omega_s$ of the spindle 124, or deployment speed, is greater when the second set of gears 118, 122 are engaged.

In some embodiments, the thumbwheel 112 and wheel axle 114 rotate in place, while the collection spindle 124 and/or the first and second driven gears 120, 122 are slidable along the longitudinal axis 126 of the collection spindle 124 from a first position to align the first set of gears 116, 120 to a second position to align the second set of gears 118, 122. The first and second driven gears 120, 122 are sufficiently spaced apart to allow one set of gears to engage while the other set of gears remains disengaged. In some embodiments, the space between the driven gears 120, 122 is at least the thickness of the thumbwheel 112 and the first and/or second actuating gears 116, 118.

In operation, the required deployment force is greatest when sheath retraction begins, such as to overcome frictional forces, including, for example, static friction. The user may choose to engage the first set of gears 116, 120 or the second set of gears 118, 122 by pushing the thumbwheel 112 from side to side along, or together with, the wheel axle 114. Thus, the user may begin by turning the thumbwheel 112 in the first position, so that the first actuating gear 116 engages the first driven gear 120 and provides a greater mechanical advantage, but results in a lower speed of sheath retraction. As the retraction wire 102 collects around the collection spindle 124, the outer sheath 104 is retracted to uncover more of the stent 170, the resisting force between the stent 170 and the outer sheath 104 decreases, and the required deployment force decreases. The user may speed up retraction by engaging the second set of gears 118, 122, when less mechanical advantage is required for the decreased deployment force. The user may also slow down retraction by switching back to engaging the first set of gears 116, 120. By allowing the user to switch between higher and lower mechanical advantage, and higher and lower retraction speed, the wire collection device 108 may provide the user more control and a more consistent and feel and touch during stent deployment.

Sheath retraction may be monitored, for example, by fluoroscopy, or with the use of radiopaque markers placed on the outer sheath 104 and inner catheter that align when retraction is complete. Alternatively, a lock or other mechanism may be configured to stop rotation of the thumbwheel 112 after a certain length of the retraction wire 102 has been collected.

In some embodiments, one or both of the shoulders 126, 128 acts as a ratchet that allows the thumbwheel 112 to rotate in one direction and prevents rotation in the opposite direction. For example, when the user releases the thumbwheel 112, the ratchet may prevent the retraction wire 102 from unwinding from the spindle 124. Alternatively, the ratchet may be a pawl and gear ratchet located on or coupled to the thumbwheel 112 or the first and/or second actuating gears 116, 118. In some embodiments, a ratchet may act directly on the retraction wire 102, for example, as with a cable tie or tie wrap. Alternatively, or additionally, the ratchet may have a high friction surface that acts on the thumbwheel 112 to prevent the thumbwheel 112 from rotating in the opposite direction. The thumbwheel 112 and collection spindle 124 may be made of rubber, plastic, metal, or other material that is sufficiently rigid to withstand the force required to turn the thumbwheel 112 and the required deployment force, and sufficiently lightweight for use in a surgical procedure. For example, the thumbwheel 112 may be formed by a two shot mold process, and/or may include materials containing acetyl or acrylonitrile butadiene styrene (ABS).

Figure 1C:
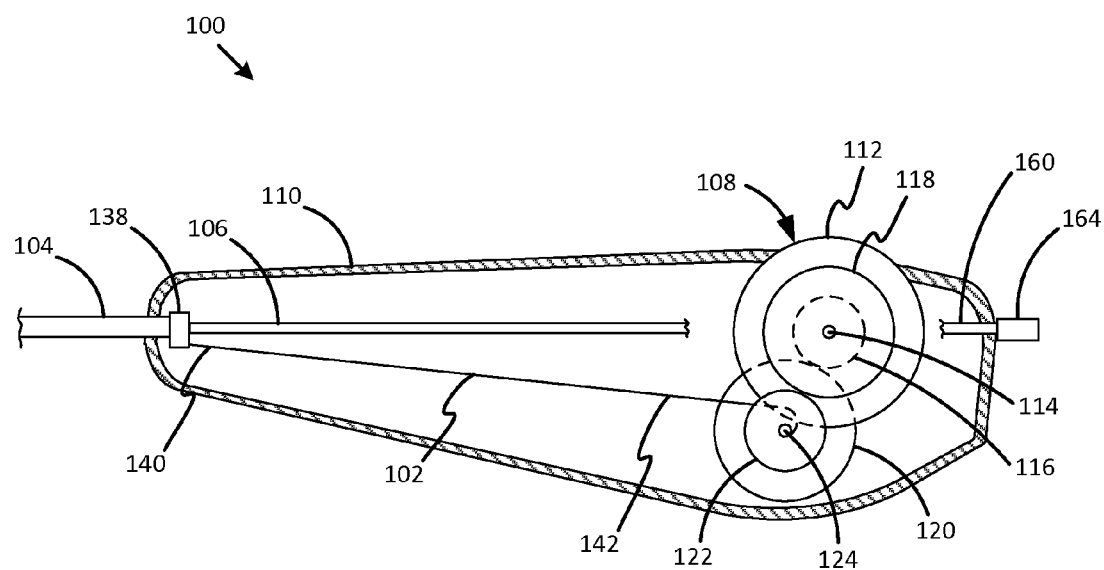
FIG. 1C is a diagrammatic longitudinal cross-sectional illustration of an exemplary wire collection device for a stent delivery system.

The initial required deployment force, or the amount of force required to begin retraction of the outer sheath 104, depends on the force required to overcome the frictional force (e.g., static friction) between the outer sheath 104 and the stent 170. The stent 170 may be located at or near a distal end 152 of the outer sheath 104 and a distal end 162 of the inner catheter 106. With reference to FIG. 1C, the proximal end 160 of the inner catheter 106 may be held in place by a known mechanism, structure, or attachment, by the housing of the handle 110. In some embodiments, the inner catheter 106 may have a proximal end 160 that protrudes through the housing of the handle 110 and may include a luer structure 164 for ease of attaching a fluid-delivery device (e.g., for delivering flushing fluid, radio-opaque contrast fluid, or other fluid), and it may also serve as a passage for a wire guide. As the outer sheath 104 begins to move, or retract, the required deployment force, or force required to continue retracting the outer sheath 104, decreases. The wire collection device 108 increases the mechanical advantage provided to the user by allowing the user to change between a higher gear ratio and a lower gear ratio. This may provide the user with a more consistent "feel" throughout the deployment of the stent, and allows the user to control the speed of retraction.

In some embodiments, the retraction wire 102 is coupled to the outer sheath 104 by a sledge 138 that is within the housing of the handle 110. Alternatively, the sledge 138 can be external to the housing, embedded in the housing, or fully or partially aligned with the housing. The inner catheter 106 extends through an aperture in the sledge 138. As the retraction wire 102 collects around the wire collection device 108, the outer sheath 104 and sledge 138 slide across the inner catheter 106, allowing the inner catheter 106 to maintain its position. Alternatively, the retraction wire 102 may be coupled to the outer sheath 104, such as by embedding the retraction wire 102 in walls of the outer sheath 104, or welding the retraction wire 102 to the outer sheath 104. The proximal end 150 of the outer sheath 104 may extend into the housing of the handle 110, or may end outside of the housing of the handle 110.

Figure 1D:
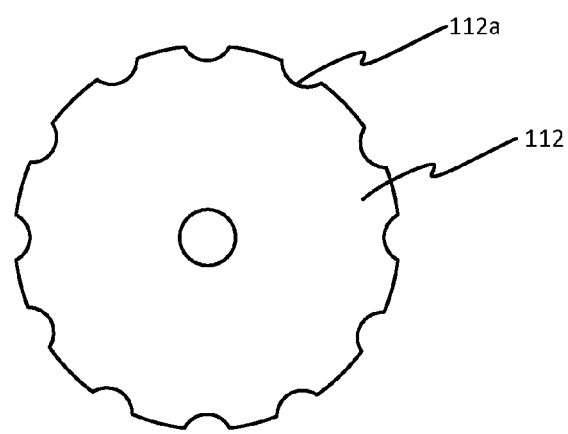
FIG. 1D is a diagrammatic illustration of a thumbwheel for an exemplary wire collection device for a stent delivery system.

With reference to FIG. 1D, the thumbwheel 112 may include notches 112a that provide grip to enable the user to turn the thumbwheel 112 more easily. Alternatively, the thumbwheel 112 may have a rough, gritty, or cross-hatched contact surface, or may be covered by or made of material, such as rubber or silicon, that provide traction to the user. For example, the thumbwheel 112 may be formed by a two shot mold process, and/or may include materials containing acetyl or acrylonitrile butadiene styrene (ABS).

Figure 4:
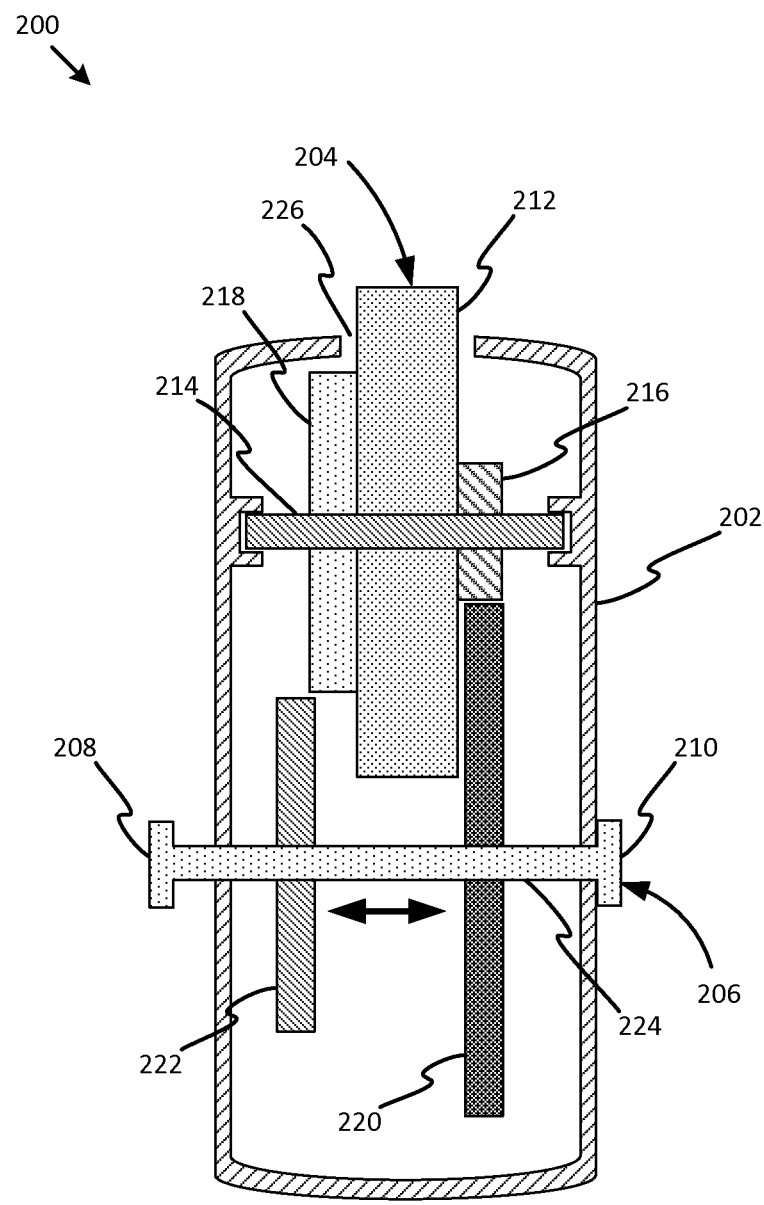
FIG. 4 is a diagrammatic illustration of an exemplary wire collection device for a stent delivery system.

In some embodiments, as illustrated with reference to FIG. 4, a wire collection device 200 includes a handle 202 that houses a thumbwheel assembly 204 and a wire collection assembly 206 with push buttons 208 and 210. The thumbwheel assembly 204 includes a thumbwheel 212 mounted on a wheel axle 214 between a first actuating gear 216 and a second actuating gear 218, and a first driven gear 220 and a second driven gear 222 mounted on a collection spindle 224. The collection spindle 224 may be substantially parallel to the wheel axle 214. The first actuating gear 216 may have a larger radius than the second driven gear 218. The wire collection assembly 206 is slidable from a first position, to align the first actuating gear 216 with the first driven gear 220, to a second position, to align the second actuating gear 218 with the second driven gear 222. The user may control or change the speed of sheath retraction, or stent deployment, by pushing on the buttons 208, 210 to change from the first set of gears 216, 220 to the second set of gears 218, 222, or from the second set of gears 218, 222 to the first set of gears 216, 220. The thumbwheel 212 is accessible through an opening 226 in the handle 202. For example, the thumbwheel 212 may be sized to partially extend through the opening 226.

When the thumbwheel 212 turns or rotates, the wire collection device 200 provides a mechanical advantage to the user that varies depending on whether the user aligns the first set of gears 216, 220 or the second set of gears 218, 222. The mechanical advantage provided depends on the gear ratio, or speed ratio, of each set of gears. For example, with reference to FIG. 4, the first actuating gear 216 has is smaller than the second actuating gear 218, and the first driven gear 220 is larger than the second driven gear 222. Then, the mechanical advantage provided to the user is the product of the gear ratio of the first set of gears 216, 220 multiplied by the ratio of the radius of the thumbwheel 212 to the radius of the collection spindle 224. Similarly, the mechanical advantage provided by the second set of gears is the product of the gear ratio of the second set of gears 218, 222 multiplied by the ratio of the radius of the thumbwheel 212 to the radius of the collection spindle 224. Because the collection spindle 224 is substantially parallel to the wheel axle 214, and the first actuating gear 216 is smaller than the second actuating gear 218, the mechanical advantage provided by the first set of gears 216, 220 is greater than the mechanical advantage provided by the second set of gears 218, 222.

During the stent deployment process, the wire collection device 200 may provide the user with improved "feel" and control of the speed of deployment. As the required deployment force varies, the user may switch between engaging the first set of gears 216, 220 and the second set of gears 218, 220 to adjust the speed of deployment. The wire collection device 200 may allow the user to speed up and slow down the speed of retraction to allow accurate placement of the stent, and to accommodate any external factors. For example, the user may need to pause the deployment process to check vital signs of the patient, or to adjust or check other equipment in an operation environment. One or both of the push buttons 208, 210 may act as ratchets to allow rotation of the wire collection assembly 204 to collect the retraction wire, and to prevent the rotation in the opposite direction so as to prevent unwinding of the retraction wire.

Figure 5:
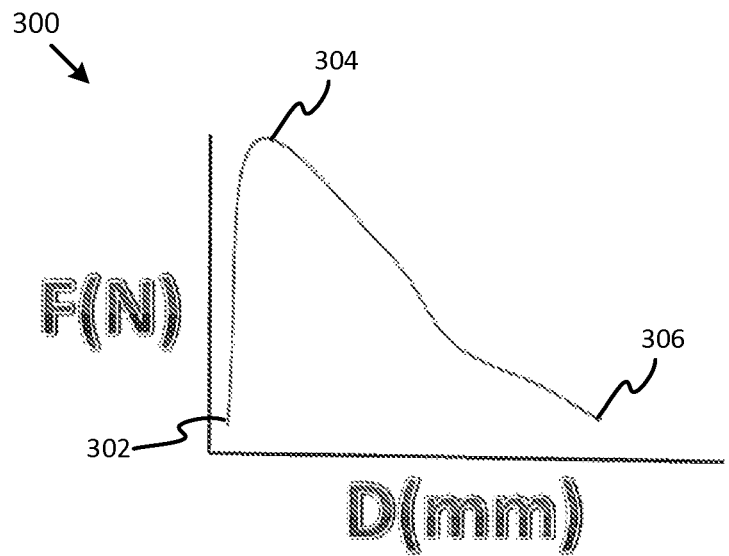
FIG. 5 is a required deployment force profile showing variation in required deployment force relative to stent deployment distance for a stent delivery system.

In some embodiments, for example, with reference to FIG. 5, a required deployment force profile 300 shows the required stent deployment force relative to the stent deployment distance (e.g., the distance of sheath retraction or length of retraction wire collected). The required deployment force increases from an initial force 302 to a threshold force 304, and decreases from the threshold force 304 to a lower force 306. The increase in required deployment force from the initial force 302 to the threshold force 304 may be the amount of force required to overcome the static friction and/or binding forces between a self-expanding stent and the outer sheath. Once the outer sheath begins to move, or retract, the required deployment force decreases from the threshold force 304 to the lower force 306, at the completion of sheath retraction. Various embodiments shown herein may be configured to accommodate change in required stent deployment force relative to the stent deployment distance, as shown in FIG. 5.

Although various embodiments of the invention have been described, it will be apparent to those of ordinary skill in the art that many more embodiments and implementations are possible that are within the scope of the invention. Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

I claim:

1. A stent deployment system, including a wire collection device comprising:
   a collection spindle rotatable to collect a retraction wire around the collection spindle, the retraction wire coupled to an outer sheath retractable to deploy a stent;
   a first driven gear and a second driven gear mounted along the collection spindle, a radius of the second driven gear being greater than a radius of the first driven gear;
   a thumbwheel mounted on a wheel axle substantially parallel to the collection spindle, the thumbwheel rotatable and disposed in mechanical communication with the wheel axle to actuate rotation of the wheel axle;
   a first actuating gear and a second actuating gear, the first actuating gear sized to engage the first driven gear to collect the retraction wire at a first speed and the second actuating gear sized to engage the second driven gear to collect the retraction wire at a second speed greater than the first speed.

2. The system of claim 1, wherein a higher gear ratio of the second driven gear relative to the second actuating gear is greater than a lower gear ratio of the first driven gear relative to the first actuating gear, thereby providing a mechanical advantage that allows collection of the retraction wire at the second speed for a consistent external force applied to turn the thumbwheel.

3. The system of claim 2, wherein the thumbwheel is slidable along the wheel axle in a first direction so as to align the first actuating gear with the first driven gear, and is slidable along the wheel axle in a second direction, opposite the first direction, so as to align the second actuating gear with the second driven gear.

4. The system of claim 2, wherein the collection spindle is slidable along a longitudinal axis of the collection spindle to align the first actuating gear with the first driven gear, and is slidable along the longitudinal axis of the collection spindle to align the second actuating gear with the second driven gear.

5. The system of claim 1, wherein the first and second actuating gears are spaced apart along the collection spindle a predetermined distance with the thumbwheel therebetween, and the first and second driven gears are spaced apart a distance greater than the predetermined distance between the first and second actuating gears.

6. The system of claim 1, wherein the first and second actuating gears form a unitary piece with the thumbwheel.

7. The system of claim 1, further comprising a ratchet to allow rotation of the collection spindle in one direction and prevent rotation of the collection spindle in an opposite direction.

8. The system of claim 1, wherein the retraction wire is coupled to the outer sheath by a sledge.

9. The system of claim 1, wherein a distal end of the retraction wire is embedded in a wall of a proximal end of the outer sheath.

10. The system of claim 1, wherein the collection spindle is further rotatable to collect an additional retraction wire around the collection spindle, the additional retraction wire coupled to the outer sheath to provide additional retraction force to deploy the stent.

11. A method for deploying a stent using the device of claim 1, the method comprising:
   turning the thumbwheel in a first position, wherein the first actuating gear engages the first driven gear to rotate the collection spindle and collect the retraction wire at the first speed;
   sliding the thumbwheel along the wheel axle into a second position until the second actuating gear is aligned with the second driven gear;
   turning the thumbwheel in the second position, wherein the second actuating gear engages the second driven gear to rotate the collection spindle and collect the retraction wire at the second speed.

12. A method for deploying a stent using the device of claim 1, the method comprising:
   turning the thumbwheel in a first position against a resisting force until the resisting force decreases, wherein the first actuating gear engages the first driven gear to provide a first level of mechanical advantage;

sliding the thumbwheel along the wheel axle into a second position until the second actuating gear is aligned with the second driven gear;

turning the thumbwheel in the second position, wherein the second actuating gear engages the second driven gear to rotate the collection spindle to provide a second level of mechanical advantage less than the first level.

13. A wire collection device for a stent deployment system, the wire collection device comprising:

a thumbwheel coupled to an axle and located between a first actuating gear and a second actuating gear, such that the thumbwheel, the first actuating gear, and the second actuating gear are rotatable about a longitudinal axis of the axle;

a wire collection spindle that is rotatable to collect a retraction wire coupled to a proximal end of an outer sheath, the wire collection spindle located a predetermined distance from the axle;

a first driven gear and a second driven gear mounted to the wire collection spindle and rotatable about a longitudinal axis of the wire collection spindle; and wherein:

a radius of the first actuating gear is greater than a radius of the second actuating gear, a radius of the first driven gear is less than a radius of the second driven gear, the thumbwheel is slidable along the longitudinal axis of the axle between a first position, wherein the first actuating gear engages the first driven gear, and a second position, wherein the second actuating gear engages the second driven gear, so as to vary a wire collection speed between a higher speed and a lower speed.

14. The device of claim 13, wherein a higher gear ratio of the second driven gear relative to the second actuating gear provides a mechanical advantage that allows collection of the retraction wire at the higher speed for a consistent external force required for collection of the retraction wire at the lower speed.

15. The device of claim 13, further comprising a ratchet that allows rotation of the thumbwheel in one direction to collect the retraction wire around the collection spindle and prevents rotation in an opposite direction.

16. The device of claim 13, wherein the thumbwheel and the first and second actuating gears form a unitary piece.

17. The device of claim 13, wherein the first and second driven gears are spaced a predetermined distance apart, and the predetermined distance is at least a combined thickness of the thumbwheel and the first and second actuating gears.

* * * * *